US011957436B2

(12) United States Patent
Tanaka et al.

(10) Patent No.: US 11,957,436 B2
(45) Date of Patent: Apr. 16, 2024

(54) LIVING BODY INTERNAL TEMPERATURE MEASURING DEVICE

(71) Applicant: Nippon Telegraph and Telephone Corporation, Tokyo (JP)

(72) Inventors: Yujiro Tanaka, Tokyo (JP); Daichi Matsunaga, Tokyo (JP); Michiko Seyama, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 779 days.

(21) Appl. No.: 17/055,218

(22) PCT Filed: May 8, 2019

(86) PCT No.: PCT/JP2019/018377

§ 371 (c)(1),
(2) Date: Nov. 13, 2020

(87) PCT Pub. No.: WO2019/220973

PCT Pub. Date: Nov. 21, 2019

(65) Prior Publication Data

US 2021/0177271 A1   Jun. 17, 2021

(30) Foreign Application Priority Data

May 16, 2018   (JP) ................................ 2018-094362

(51) Int. Cl.
*A61B 5/01*   (2006.01)
*A61B 8/08*   (2006.01)
(Continued)

(52) U.S. Cl.
CPC .............. *A61B 5/01* (2013.01); *A61B 8/5207* (2013.01); *G01K 11/22* (2013.01); *G01K 13/20* (2021.01); *G01S 7/52085* (2013.01)

(58) Field of Classification Search
CPC . A61B 5/01; A61B 8/00; G01K 11/20; G01K 13/20; G01K 11/22
See application file for complete search history.

(56) References Cited

U.S. PATENT DOCUMENTS

| 4,754,760 | A | * | 7/1988 | Fukukita | ............... | A61B 8/5223 |
| | | | | | | 600/549 |
| 2005/0281313 | A1 | * | 12/2005 | Qian | ...................... | G01K 11/22 |
| | | | | | | 702/131 |
| 2006/0241436 | A1 | * | 10/2006 | Sunnanvader | ........... | A61B 5/01 |
| | | | | | | 600/438 |

OTHER PUBLICATIONS

Amini et al. Noninvasive Estimation of Tissue Temperature Via High-Resolution Spectral Analysis Techniques. IEEE Transactions on Biomedical Engineering, vol. 52, No. 2, Feb. 2005. Doi: 10.1109/TBME.2004.840189. (Year: 2005).*

(Continued)

*Primary Examiner* — Angela M Hoffa
*Assistant Examiner* — Younhee Choi
(74) *Attorney, Agent, or Firm* — Slater Matsil, LLP

(57) ABSTRACT

A device includes: an ultrasonic wave irradiation unit that irradiates a living body with an ultrasonic wave; an ultrasonic wave detection unit that receives an ultrasonic wave reflected by the living body; and a calculation unit that calculates an amount of temperature change in the living body. The calculation unit is configured to: calculate a frequency of an ultrasonic wave amplified in the living body, based on information on a structure of the living body; perform frequency analysis on the ultrasonic wave received by the ultrasonic wave detection unit and acquire an amplitude spectrum of the ultrasonic wave; identify, from the amplitude spectrum, a peak frequency closest to the frequency of the ultrasonic wave; calculate an amount of frequency change, from two peak frequencies identified by ultrasonic wave irradiations in twice; and calculate an (Continued)

amount of temperature change in the living body from the amount of frequency change.

10 Claims, 10 Drawing Sheets

(51) Int. Cl.
*G01K 11/22* (2006.01)
*G01K 13/20* (2021.01)
*G01S 7/52* (2006.01)

(56) References Cited

OTHER PUBLICATIONS

Maass-Moren et al. Noninvasive temperature estimation in tissue via ultrasound echo-shifts. Part I. Analytical model. J. Acoust. Soc. Am. Oct. 1, 1996; 100 (4): 2514-2521. https://doi.org/10.1121/1.417359. (Year: 1996).*

Nakagawa et al., "Proposal of Wearable Deep Thermometer with MEMS Thermal Flow Easting Sensor," Journal E of the Institute of Electrical Engineers of Japan (Journal of Sensor and Micromachine Division), vol. 135, No. 8, Feb. 9, 2015, pp. 343-348.

* cited by examiner

LIVING BODY INTERNAL TEMPERATURE MEASURING DEVICE

CROSS-REFERENCE TO RELATED APPLICATIONS

This application is a national phase entry of PCT Application No. PCT/JP2019/018377, filed on May 8, 2019, which claims priority to Japanese Application No. 2018-094362, filed on May 16, 2018, which applications are hereby incorporated herein by reference.

TECHNICAL FIELD

The present invention relates to an in-vivo temperature measurement device that detects a temperature change in a living body.

BACKGROUND

In recent years, asocial jet-lag has become a problem. The social jet-lag may cause various physical and mental disorders due to inconsistency between a social time and a biological clock or a biorhythm of each person who lives a life, and may lead to lifestyle diseases. A human's biological clock can be known from various endocrine substances or vital information. Measurement of the endocrine substances requires several hours, resulting in imposing a burden on a research subject mentally and physically.

On the other hand, it is known that a human's biorhythm is usefully grasped by measuring a change in deep body temperature as vital information. When a depth exceeds a certain depth from the skin to the core, a temperature region not being affected by a change in outside air temperature exists, and a temperature at such a region is called a deep body temperature (core temperature). Examples of methods of measuring the deep body temperature include a method of inserting a probe of a thermometer into a body and a method of swallowing the thermometer, but all of the methods may have hygiene problems and may also impose a burden on a research subject mentally and physically. Therefore, methods of measuring the temperature with a non-invasive manner from the outside of the body are demanded, and it can be said that a percutaneous temperature measurement method is particularly useful in terms of easy and daily body temperature management. For example, it is useful to measure the temperature at a core site of the living body, for example, rectal temperature.

Conventionally, a thermometer using a MEMS heat flux sensor has been proposed as a means for percutaneously measuring a deep body temperature (see Non-Patent Literature 1). However, the percutaneous thermometer may be difficult to grasp the change in deep body temperature without delay. The reason why the percutaneous thermometer is difficult to grasp the change in deep body temperature is that there is a delay time until the deep body temperature is reflected in the skin, the delay time changes due to a change in blood flow, and a skin temperature changes due to outside air.

CITATION LIST

Non-Patent Literature

Non-Patent Literature 1: Shinya Nakagawa, et al., "Wearable core temperature thermometer implemented by the MEMS heat flux sensor", The transactions of the Institute of Electrical Engineers of Japan E, Vol. 135, No. 8, p. 343-348, 2015.

SUMMARY

Technical Problem

Embodiments of the present invention have been made to solve the above problems, and an object thereof is to provide an in-vivo temperature measurement device capable of grasping a temperature change in a living body without delay.

Means for Solving the Problem

An in-vivo temperature measurement device of embodiments of the present invention includes: an ultrasonic wave irradiation unit that irradiates a living body with an ultrasonic wave; an ultrasonic wave detection unit that receives an ultrasonic wave reflected by the living body; a frequency calculation portion that calculates a frequency of an ultrasonic wave amplified in the living body, based on information on a structure of the living body; a frequency analysis portion that performs frequency analysis on the ultrasonic wave received by the ultrasonic wave detection unit and acquires an amplitude spectrum of the ultrasonic wave; a frequency identification portion that identifies, from the amplitude spectrum, a peak frequency closest to the frequency calculated by the frequency calculation portion; a frequency change calculation portion that calculates an amount of frequency change, from two peak frequencies identified by ultrasonic wave irradiations in twice; and a temperature change calculation portion that calculates an amount of temperature change in the living body from the amount of frequency change.

An in-vivo temperature measurement device of embodiments of the present invention includes: an ultrasonic wave irradiation unit that irradiates a living body with an ultrasonic wave; an ultrasonic wave detection unit that receives an ultrasonic wave reflected by the living body; a frequency calculation portion that calculates a frequency of an ultrasonic wave amplified in the living body, based on information on a structure of the living body; an ultrasonic wave irradiation control portion that sweeps a repetition frequency at which an ultrasonic wave is emitted from the ultrasonic wave irradiation unit within a predetermined range centered on the frequency calculated by the frequency calculation portion; a lock-in detector that detects an ultrasonic wave of the repetition frequency from the ultrasonic waves received by the ultrasonic wave detection unit; an amplitude spectrum acquisition portion that collects amplitude values of signals sequentially output from the lock-in detector and acquires an amplitude spectrum of the ultrasonic wave; a frequency identification portion that identifies, from the amplitude spectrum, a peak frequency closest to the frequency calculated by the frequency calculation portion; a frequency change calculation portion that calculates an amount of frequency change from two peak frequencies obtained by sweeping the repetition frequency twice; and a temperature change calculation portion that calculates an amount of temperature change in the living body from the amount of frequency change.

An in-vivo temperature measurement device of embodiments of the present invention includes: an ultrasonic wave irradiation unit that irradiates a living body with an ultrasonic wave; an ultrasonic wave detection unit that receives an ultrasonic wave reflected by the living body; a frequency calculation portion that calculates a frequency of an ultrasonic wave amplified in the living body, based on information on a structure of the living body; an ultrasonic wave irradiation control portion that sweeps a repetition frequency at which an ultrasonic wave is emitted from the ultrasonic wave irradiation unit within a predetermined range centered on the frequency calculated by the frequency calculation portion; a lock-in detector that detects a phase of an ultrasonic wave of the repetition frequency from the ultrasonic waves received by the ultrasonic wave detection unit; a phase spectrum acquisition portion that collects phase values sequentially output from the lock-in detector and acquires a phase spectrum of the ultrasonic wave; a phase identification portion that identifies, from the phase spectrum, a phase of a peak frequency of an amplitude spectrum of the ultrasonic wave; a phase change calculation portion that calculates an amount of phase change from phases of two peak frequencies obtained by sweeping the repetition frequency twice; and a temperature change calculation portion that calculates an amount of temperature change in the living body from the amount of phase change.

In one configuration example of the in-vivo temperature measurement device of embodiments of the present invention, the frequency calculation portion calculates a frequency of an ultrasonic wave amplified in the living body, based on the information on the structure of the living body and a value of a sound speed in the living body, the value of the sound speed being registered in advance.

In one configuration example of the in-vivo temperature measurement device of embodiments of the present invention, the information on the structure of the living body is a distance between structures in the living body.

Effects of Embodiments of the Invention

According to embodiments of the present invention, it is possible to estimate the amount of temperature change in the living body and to non-invasively obtain the temperature change in the living body that is changing every moment, without being affected by the outside air or the skin temperature, by irradiating the living body with the ultrasonic wave, performing the frequency analysis on the ultrasonic wave received by the ultrasonic wave detection unit and acquiring the amplitude spectrum of the ultrasonic wave, and calculating the amount of frequency change from two peak frequencies identified by ultrasonic wave irradiations in twice.

According to embodiments of the present invention, it is possible to estimate the amount of temperature change in the living body and to non-invasively obtain the temperature change in the living body that is changing every moment, without being affected by the outside air or the skin temperature, by irradiating the living body with the ultrasonic wave while sweeping the repetition frequency, detecting the ultrasonic wave of the repetition frequency from the ultrasonic waves received by the ultrasonic wave detection unit to acquire the amplitude spectrum of the ultrasonic wave, and calculating the amount of frequency change from two peak frequencies obtained by sweeping the repetition frequency twice.

According to embodiments of the present invention, it is possible to estimate the amount of temperature change in the living body and to non-invasively obtain the temperature change in the living body that is changing every moment, without being affected by the outside air or the skin temperature, by irradiating the living body with the ultrasonic wave while sweeping the repetition frequency, detecting the phase of the ultrasonic wave of the repetition frequency from the ultrasonic waves received by the ultrasonic wave detection unit to acquire the phase spectrum of the ultrasonic wave, and calculating the amount of phase change from phases of two peak frequencies obtained by sweeping the repetition frequency twice.

DETAILED DESCRIPTION OF ILLUSTRATIVE EMBODIMENTS

First Embodiment

Figure 1:
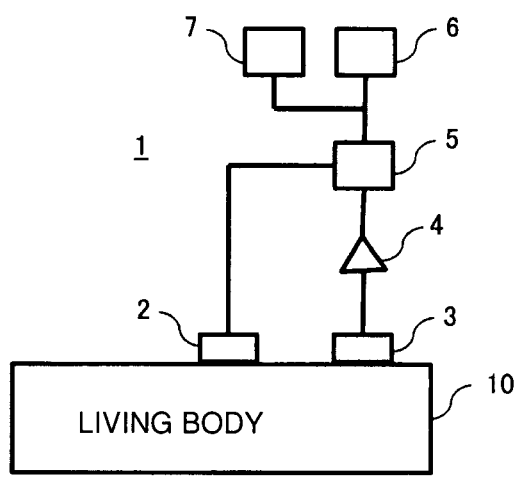
FIG. 1 is a block diagram showing a configuration of an in-vivo temperature measurement device according to a first embodiment of the present invention.

Embodiments of the present invention will be described below with reference to the drawings. FIG. 1 is a block diagram showing a configuration of an in-vivo temperature measurement device according to a first embodiment of the present invention. The in-vivo temperature measurement device 1 includes an ultrasonic wave irradiation unit 2 that irradiates a living body 10 with ultrasonic waves, an ultrasonic wave detection unit 3 that receives the ultrasonic waves returned from the living body 10, an amplifier 4 that amplifies an electric signal obtained from the ultrasonic wave detection unit 3, a calculation unit 5 that calculates the amount of temperature change in the living body 10 based on the output of the amplifier 4, a storage unit 6 that stores various data and calculation results necessary for calculation, and a communication unit 7 that communicates with an external device.

Figure 2:
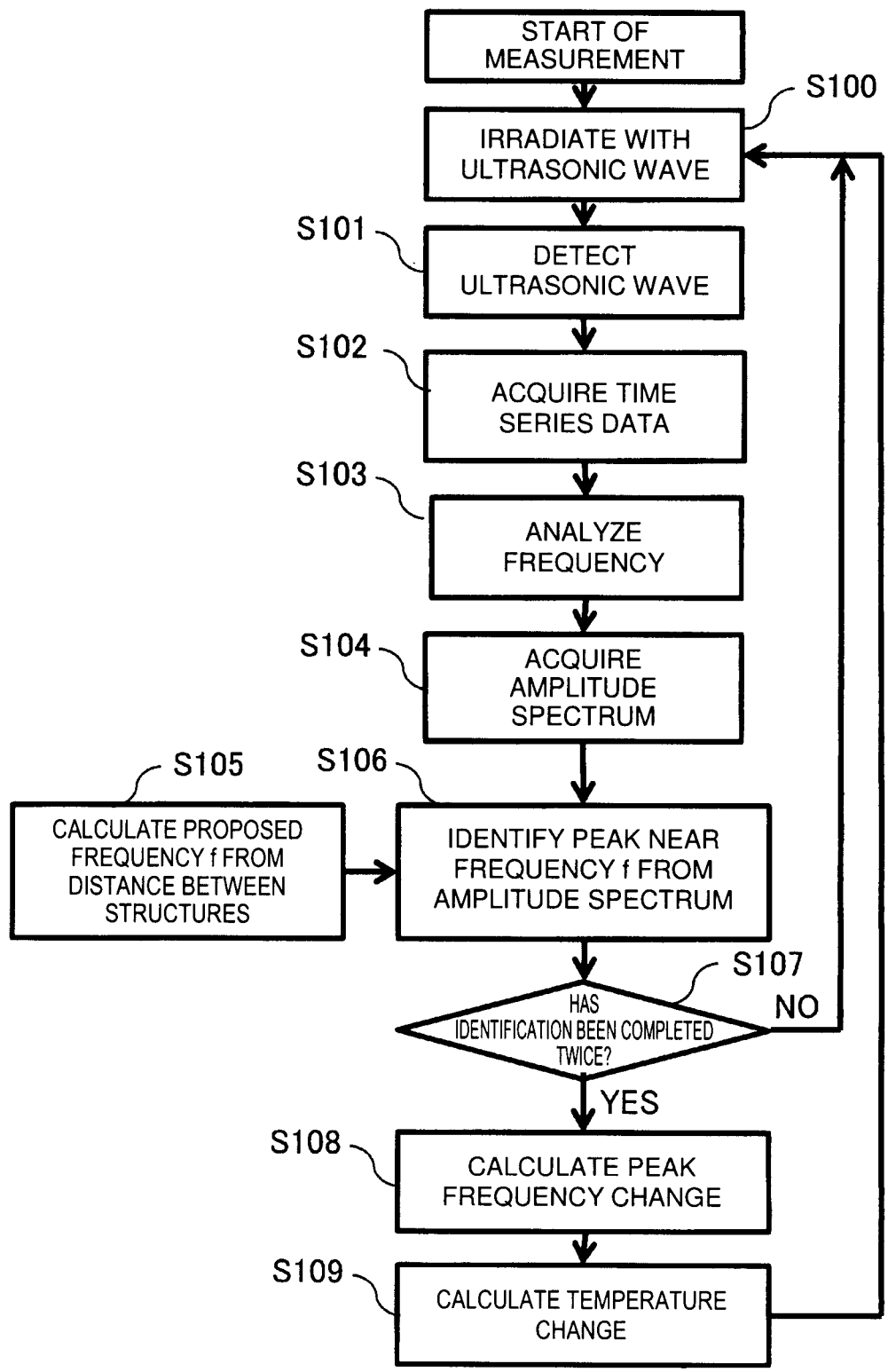
FIG. 2 is a flowchart for describing an operation of the in-vivo temperature measurement device according to the first embodiment of the present invention.
Figure 3:
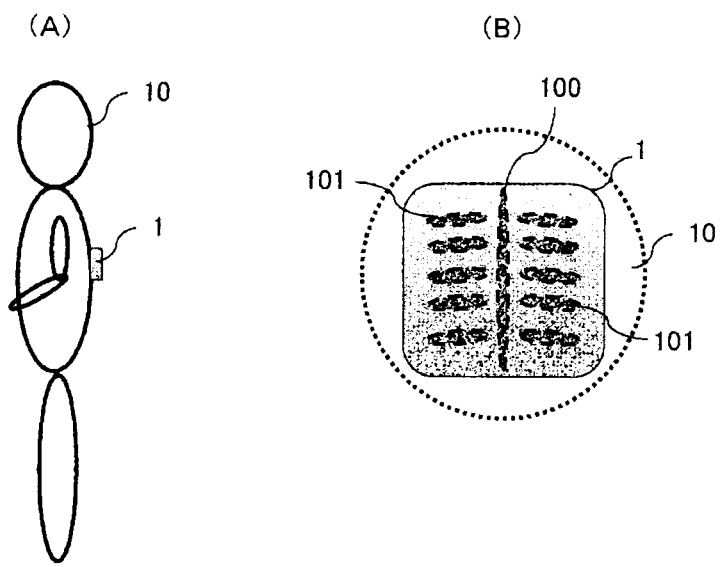
FIG. 3 is a view for describing an in-vivo temperature measurement method using the in-vivo temperature measurement device according to the first embodiment of the present invention.

FIG. 2 is a flowchart for describing an operation of the in-vivo temperature measurement device 1 of the present embodiment, and FIGS. 3(A) and 3(B) are views for describing an in-vivo temperature measurement method using the in-vivo temperature measurement device 1 of the present embodiment. FIG. 3(A) is a side view showing a positional relation between the in-vivo temperature measurement device 1 and the living body 10, and FIG. 3(B) is a rear view. In FIG. 3(B), reference numeral 100 indicates a spine of the living body 10, and reference numeral 101 indicates ribs.

In the present embodiment, the in-vivo temperature measurement device 1 is disposed such that a transmission/reception surface of the in-vivo temperature measurement device 1 provided with the ultrasonic wave irradiation unit 2 and the ultrasonic wave detection unit 3 comes in contact with a site on a back of the living body 10 (human body) at an approximate rib-height level (see FIGS. 3(A) and 3(B)).

The ultrasonic wave irradiation unit 2 irradiates the living body 10 with ultrasonic waves (step S100 in FIG. 2). The ultrasonic wave detection unit 3 receives the ultrasonic wave returned from the living body 10 (step S101 in FIG. 2).

Figure 4:
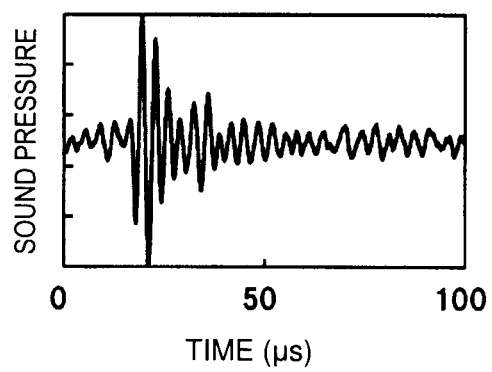
FIG. 4 is a view showing an example of a waveform of an ultrasonic wave reception signal detected by an ultrasonic wave detection unit of the in-vivo temperature measurement device according to the first embodiment of the present invention.

FIG. 4 shows an example of a waveform of an ultrasonic wave reception signal detected by the ultrasonic wave detection unit 3. The amplifier 4 amplifies the ultrasonic wave reception signal detected by the ultrasonic wave detection unit 3.

Figure 5:
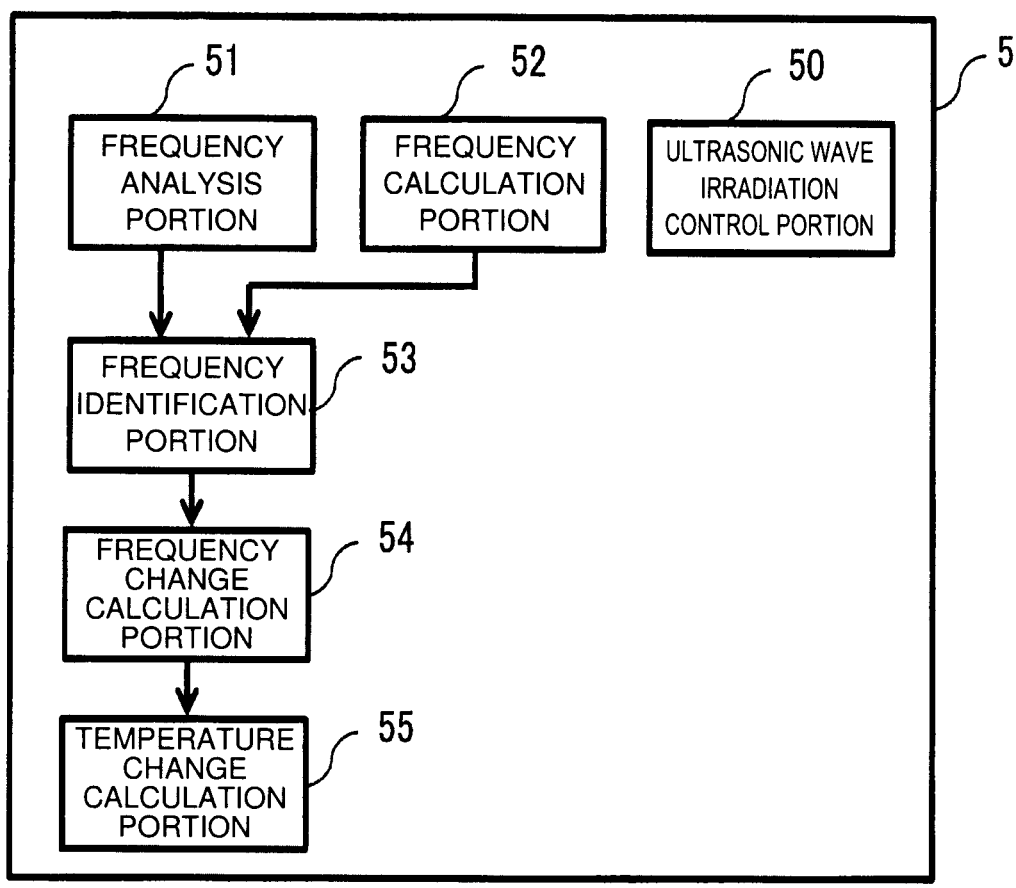
FIG. 5 is a block diagram showing a configuration example of a calculation unit of the in-vivo temperature measurement device according to the first embodiment of the present invention.

FIG. 5 is a block diagram showing a configuration example of the calculation unit 5. The calculation unit 5 includes an ultrasonic wave irradiation control portion 50, a frequency analysis portion 51, a frequency calculation portion 52, a frequency identification portion 53, a frequency change calculation portion 54, and a temperature change calculation portion 55.

Figure 6:
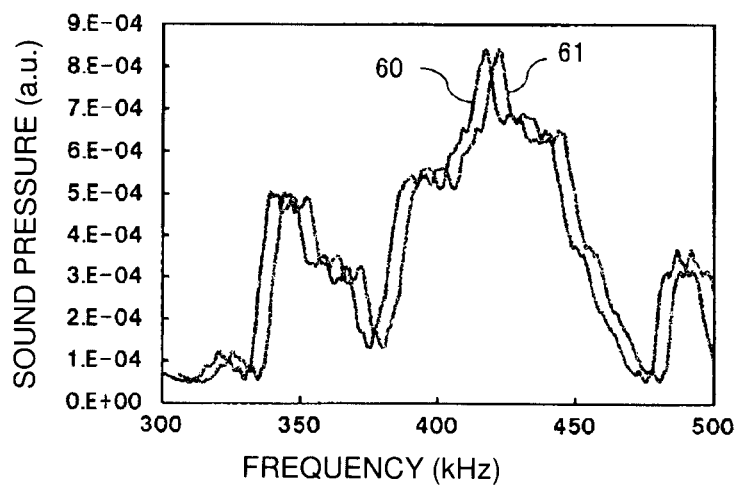
FIG. 6 is a view showing an example of an amplitude spectrum of the ultrasonic wave reception signal.

The frequency analysis portion 51 of the calculation unit 5 acquires time change data (time series data) of the ultrasonic wave reception signal detected by the ultrasonic wave detection unit 3 and amplified by the amplifier 4 (step S102 in FIG. 2), and obtains an amplitude spectrum of the ultrasonic wave reception signal by performing frequency analysis on the time series data by a method such as FFT (Fast Fourier Transform) (step S103, S104 in FIG. 2). FIG. 6 shows an example of the amplitude spectrum of the ultrasonic wave reception signal obtained by the frequency analysis portion 51. In FIG. 6, reference numeral 60 indicates a first measurement result, and reference numeral 61 indicates a second measurement result, for example.

As is clear from FIG. 6, the ultrasonic waves emitted from the ultrasonic wave irradiation unit 2 have various frequency components. The ultrasonic waves are reflected and scattered in the living body 10, but become a peak at various frequencies depending on the shape of the living body 10 and in-vivo structures such as internal organs and bones. In particular, sound waves are strongly reflected at a place where acoustic impedance is largely different. Therefore, sound waves amplified by repeating reflection between bones having different biological tissues and acoustic impedances are strongly observed. Frequencies of the sound waves to be observed are different from each other depending on the distance between bones and tissues such as fat and muscle. In other words, the different in the frequency of the sound waves is due to a difference in a speed of sound. The speed of sound also changes with a temperature, and the distance between bones and the tissues such as fat and muscle do not change with time. Therefore, the change in the peak frequency of the ultrasonic waves to be observed reflects the temperature change inside the living body 10, and the amount of frequency change corresponds to a change amount of deep body temperature.

As shown in FIGS. 3(A) and 3(B), when the in-vivo temperature measurement device 1 is disposed at the site on the back of the living body 10 (human body) at an approximate rib-height level, the ultrasonic waves emitted from the ultrasonic wave irradiation unit 2 are repeatedly reflected between the ribs of the living body 10, and the ultrasonic waves of an appropriate frequency are amplified. When a distance between the ribs is defined as L and the speed of sound when a temperature is T is defined as V(T), a frequency f of the sound wave amplified by the reflection between the ribs is generally given by the following formula.

Formula 1

$$f = \frac{V(T)}{nL} \tag{1}$$

Figure 7:
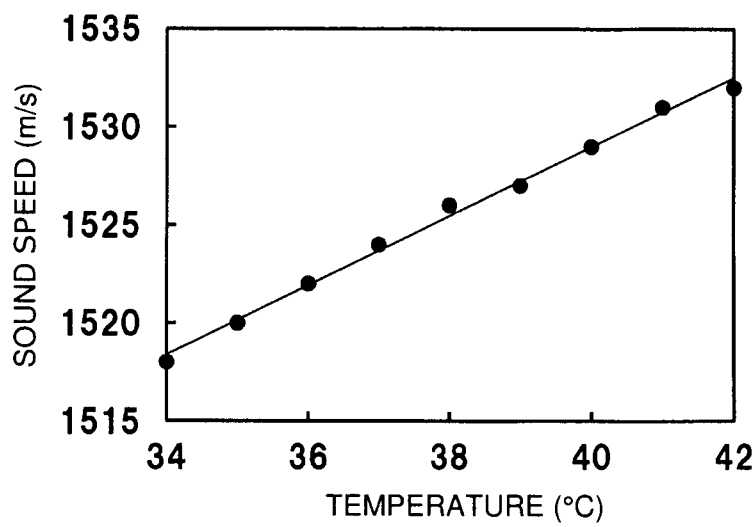
FIG. 7 is a view showing an example of a relation between a temperature and a speed of sound.
Figure 8:
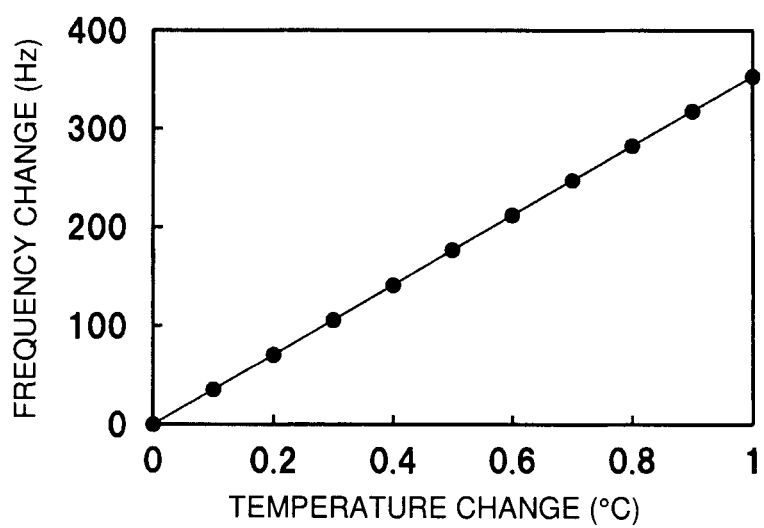
FIG. 8 is a view showing an example of a relation between a temperature change and a frequency change of a sound wave.

In Formula (1), n is a fixed number. When an average speed of sound V in the living body 10 is 1490 m/s and the distance L between the ribs is 1 cm, an ultrasonic wave having a frequency of approximately 298 kHz and an ultrasonic wave having a frequency of an integral multiple thereof are amplified. The living body is composed of various tissues, but a typical ingredient of the living body is water. As shown in FIG. 7, the speed of sound V in water changes almost linearly with the temperature T. In this way, a relation between a temperature change ΔT and a frequency change Δf of the sound wave when the speed of sound V changes linearly with the temperature T changes as shown in FIG. 8 according to the following formula.

Formula 2

$$\Delta f \propto \frac{\Delta T}{nL} \tag{2}$$

The ultrasonic waves emitted from the ultrasonic wave irradiation unit 2 are reflected and scattered in the living body 10, some of the ultrasonic wave is observed by the ultrasonic wave detection unit 3, and an amplitude spectrum as shown in FIG. 6 is obtained by the frequency analysis described above. An amplitude spectrum denoted by 60 in FIG. 6 indicates an amplitude spectrum before the temperature in the living body 10 changes, and amplitude spectrum denoted by 61 in FIG. 6 indicates an amplitude spectrum after the temperature inside the living body 10 changes. As described above, when the ultrasonic wave is amplified in the living body 10, a peak appears in the amplitude spectrum.

As is clear from Formula (2) and FIG. 6, when the temperature inside the living body 10 changes by ΔT, a peak frequency of the amplitude spectrum changes by Δf. At this time, a relation between the temperature change ΔT in the living body 10 and the peak frequency change Δf of the amplitude spectrum is expressed by the following formula.

Formula 3

$$\Delta f = C \Delta T \quad (3)$$

In Formula (3), C is a fixed number. Thus, when the peak frequency change Δf of the amplitude spectrum can be obtained, it can be understood that the temperature change ΔT in the living body 10 can be estimated. As for the ultrasonic waves, since the higher the frequency, the greater the attenuation, not harmonic waves that are integral multiples of a fundamental sound, but a fundamental sound defined by Formula (1) may be used. The peak frequency change Δf of the amplitude spectrum is affected by the proportion of fat in the living body 10, but the temperature change ΔT in the living body 10 and the peak frequency change Δf can obtain a substantially linear response. Further, the peak frequency change Δf changes depending on the distance between structures in the living body 10, but as described above, the temperature change ΔT and the frequency change Δf can obtain a substantially linear response.

Specific processing in the present embodiment is as follows. The frequency calculation portion 52 of the calculation unit 5 calculates the frequency f of the ultrasonic wave amplified in the living body 10 using Formula (1) (step S105 in FIG. 2). At this time, since the temperature inside the living body 10 is undetermined, the frequency calculation portion 52 uses the average speed of sound V in the living body 10 instead of the speed of sound V(T) when the temperature is T. The value of the speed of sound V, the value of the distance L between the structures in the living body 10 (referred to as the distance between the ribs in the present embodiment), and the fixed number n are registered in the storage unit 6 in advance. The value of the fixed number n can be determined, for example, by previous experiment in which the living body is irradiated with ultrasonic waves and the peak frequency of the amplitude spectrum of the ultrasonic waves is obtained.

The frequency identification portion 53 of the calculation unit 5 identifies a peak frequency closest to the frequency f calculated by the frequency calculation portion 52, from the amplitude spectrum obtained by the frequency analysis portion 51 (step S106 in FIG. 2). Then, the calculation unit 5 returns to step S100 when the identification of the peak frequency in step S106 has not been completed twice (NO in step S107 in FIG. 2). In this way, the processes of steps S100 to S104 and S106 are repeated twice.

The frequency change calculation portion 54 of the calculation unit 5 calculates the amount of peak frequency change Δf, that is, a difference Δf (=f2−f1) between a second peak frequency f2 and a first peak frequency f1 obtained by the frequency identification portion 53 (step S108 in FIG. 2).

Then, the temperature change calculation portion 55 of the calculation unit 5 calculates, from the amount of peak frequency change Δf, the amount of temperature change ΔT in the living body 10 using Formula (3) (step S109 in FIG. 2). The fixed number C is registered in the storage unit 6 in advance. Note that the value of the fixed number C can be determined by, for example, previous experiment in which a probe of a thermometer is inserted into the living body to obtain a change in deep body temperature.

The value of the amount of temperature change ΔT calculated by the temperature change calculation portion 55 is transmitted to the outside via the communication unit 7. In this way, the in-vivo temperature measurement device 1 repeats the processes of steps S100 to S104 and S106 to S109 until a user gives an instruction to stop the measurement.

Figure 9:
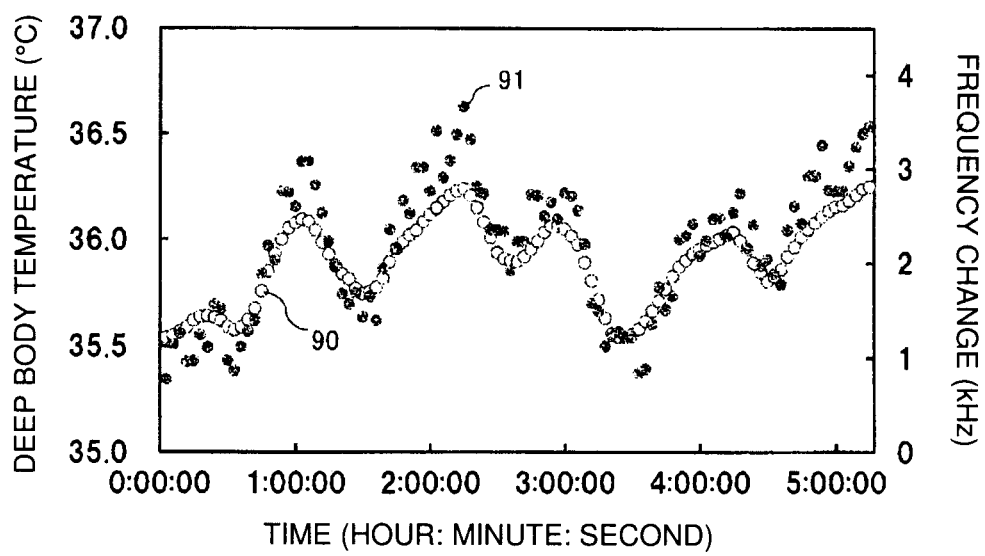
FIG. 9 is a view for describing an effect of the in-vivo temperature measurement device according to the first embodiment of the present embodiment.

FIG. 9 is a view for describing the effect of the present embodiment. In FIG. 9, reference numeral 90 indicates the deep body temperature in the living body obtained by insertion of the probe of the thermometer into the living body, and reference numeral 91 indicates the peak frequency change obtained in the present embodiment. It can be seen from FIG. 9 that the change in the deep body temperature and the peak frequency change fully coincide with each other.

Second Embodiment

Figure 10:
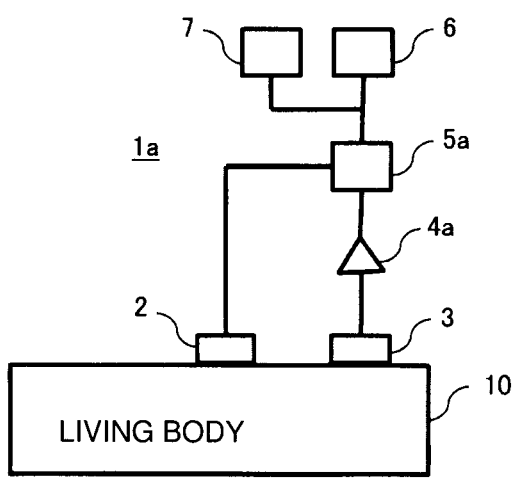
FIG. 10 is a block diagram showing a configuration of an in-vivo temperature measurement device according to a second embodiment of the present invention.

A second embodiment of the present invention will be described below. FIG. 10 is a block diagram showing a configuration of an in-vivo temperature measurement device according to the second embodiment of the present invention, and the same components as those in FIG. 1 are denoted by the same reference numerals. An in-vivo temperature measurement device 1a of the present embodiment includes an ultrasonic wave irradiation unit 2, an ultrasonic wave detection unit 3, a lock-in detector 4a, a calculation unit 5a, a storage unit 6, and a communication unit 7.

Figure 11:
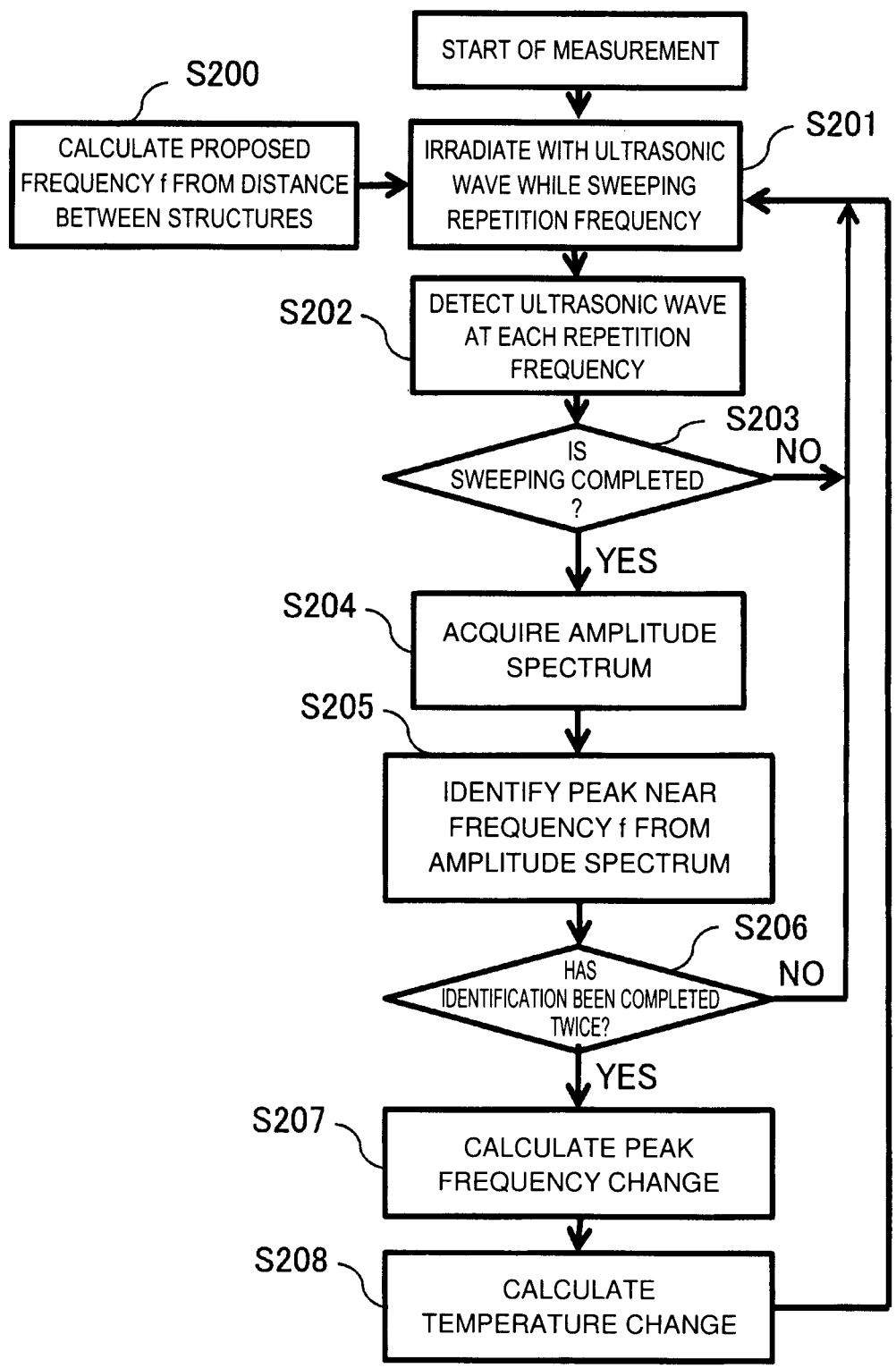
FIG. 11 is a flowchart for describing an operation of the in-vivo temperature measurement device according to the second embodiment of the present invention.
Figure 12:
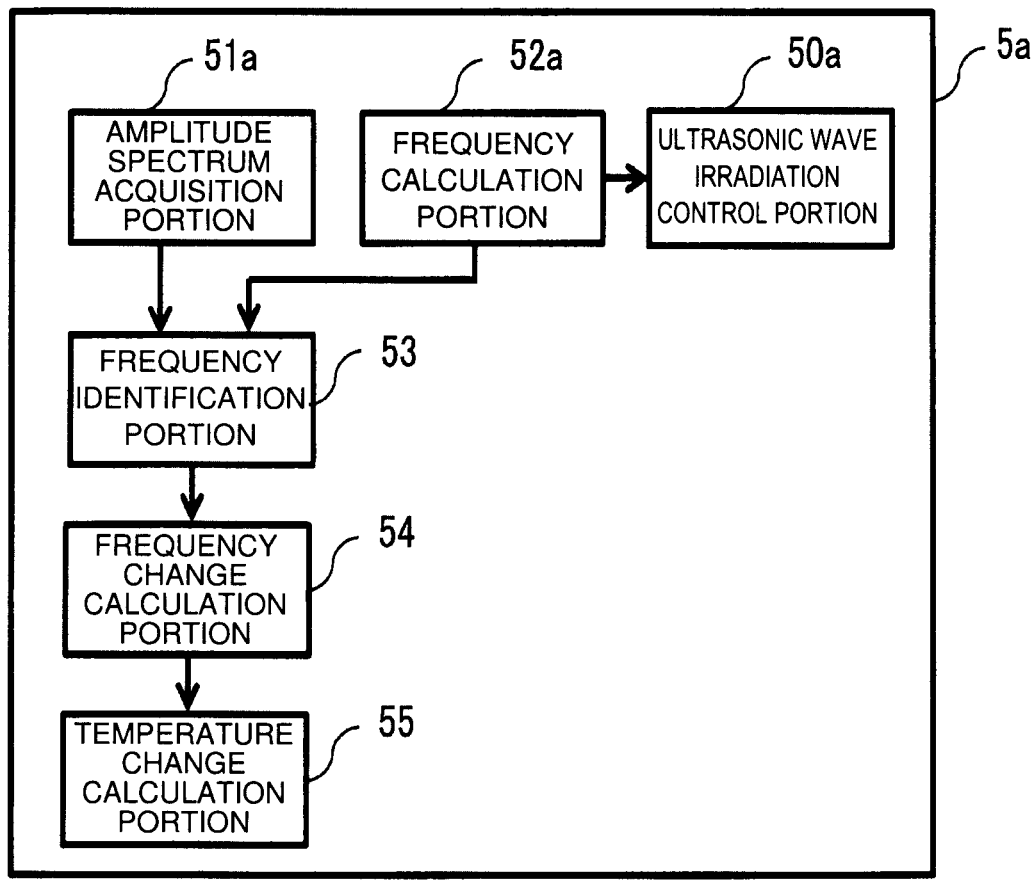
FIG. 12 is a block diagram showing a configuration example of a calculation unit of the in-vivo temperature measurement device according to the second embodiment of the present invention.

FIG. 11 is a flowchart for describing an operation of the in-vivo temperature measurement device 1a of the present embodiment, and FIG. 12 is a block diagram showing a configuration example of the calculation unit 5a of the present embodiment. The calculation unit 5a includes an ultrasonic wave irradiation control portion 50a, an amplitude spectrum acquisition portion 51a, a frequency calculation portion 52a, a frequency identification portion 53, a frequency change calculation portion 54, and a temperature change calculation portion 55.

In the present embodiment, first, the frequency calculation portion 52a of the calculation unit 5a calculates a frequency f of an ultrasonic wave amplified in the living body 10 as in step S106 (step S200 in FIG. 11).

In the first embodiment, the ultrasonic wave irradiation control portion 50 of the calculation unit 5 only needs to control the ultrasonic wave irradiation unit 2 to transmit the ultrasonic wave. On the other hand, the ultrasonic wave irradiation control portion 50a of the present embodiment sweeps a repetition frequency, at which the ultrasonic wave is emitted from the ultrasonic wave irradiation unit 2, within a range of frequency f±α (α is a predetermined width) calculated by the frequency calculation portion 52a (step S201 in FIG. 11).

The lock-in detector (phase amplifier) 4a detects an ultrasonic wave reception signal having the above-described repetition frequency from the ultrasonic wave reception signals obtained by the ultrasonic wave detection unit 3 (step S202 in FIG. 11).

Thus, by emitting the ultrasonic wave while sweeping the repetition frequency to detect the ultrasonic wave reception signal at each repetition frequency and collecting an amplitude value (sound pressure) of the signal to be sequentially output from the lock-in detector 4a, the amplitude spectrum acquisition portion 51a can acquire an amplitude spectrum of the ultrasonic wave reception signal (step S204 in FIG. 11). The amplitude spectrum obtained at this time is similar to the amplitude spectrum shown in FIG. 6, for example.

The frequency identification portion 53 of the calculation unit 5a identifies a peak frequency closest to the frequency f calculated by the frequency calculation portion 52a, from the amplitude spectrum acquired by the amplitude spectrum acquisition portion 51a (step S205 in FIG. 11).

Operations (steps S206 to S208 in FIG. 11) of the frequency change calculation portion 54 and the temperature change calculation portion 55 are as described in steps S107 to S109.

The in-vivo temperature measurement device 1a repeats the processes of steps S201 to S208 until a user gives an instruction to stop the measurement, for example. Thus, it is possible to obtain an effect of the present embodiment similar to that of the first embodiment.

Third Embodiment

Figure 13:
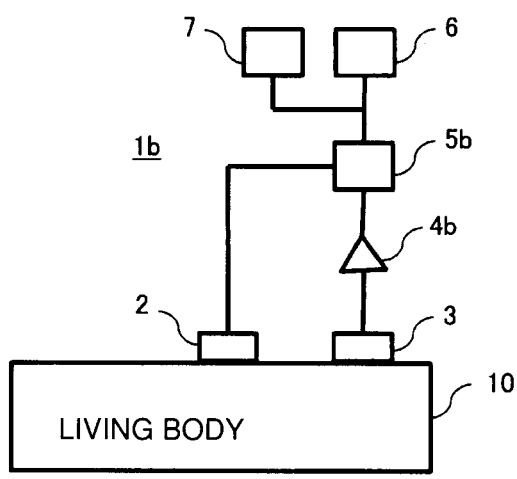
FIG. 13 is a block diagram showing a configuration of an in-vivo temperature measurement device according to a third embodiment of the present invention.

A third embodiment of the present invention will be described below. FIG. 13 is a block diagram showing a configuration of an in-vivo temperature measurement device according to the third embodiment of the present invention, and the same components as those in FIGS. 1 and 10 are denoted by the same reference numerals. An in-vivo temperature measurement device 1b of the present embodiment includes an ultrasonic wave irradiation unit 2, an ultrasonic wave detection unit 3, a lock-in detector 4b, a calculation unit 5b, a storage unit 6, and a communication unit 7.

Figure 14:
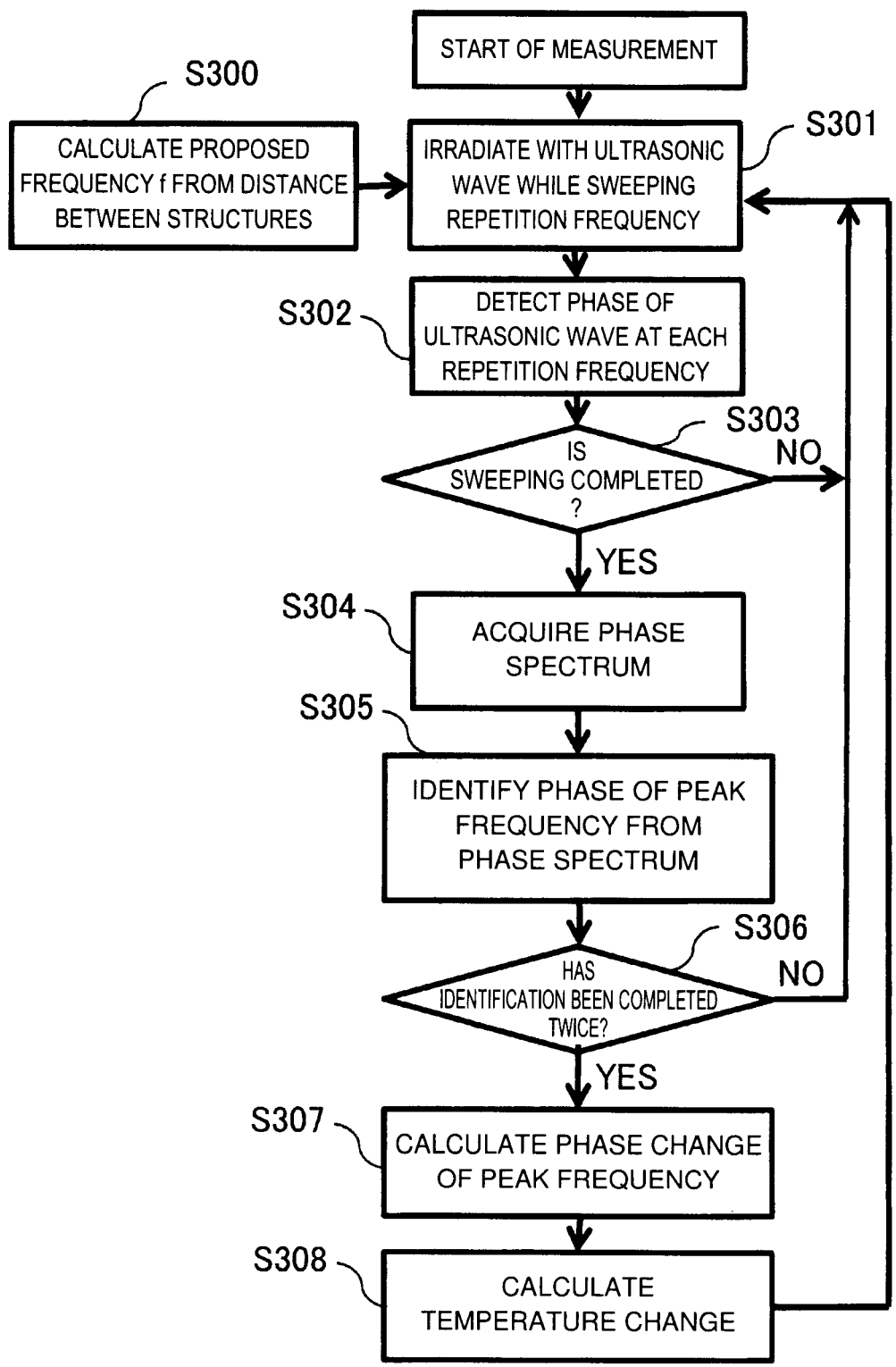
FIG. 14 is a flowchart for describing an operation of the in-vivo temperature measurement device according to the third embodiment of the present invention.
Figure 15:
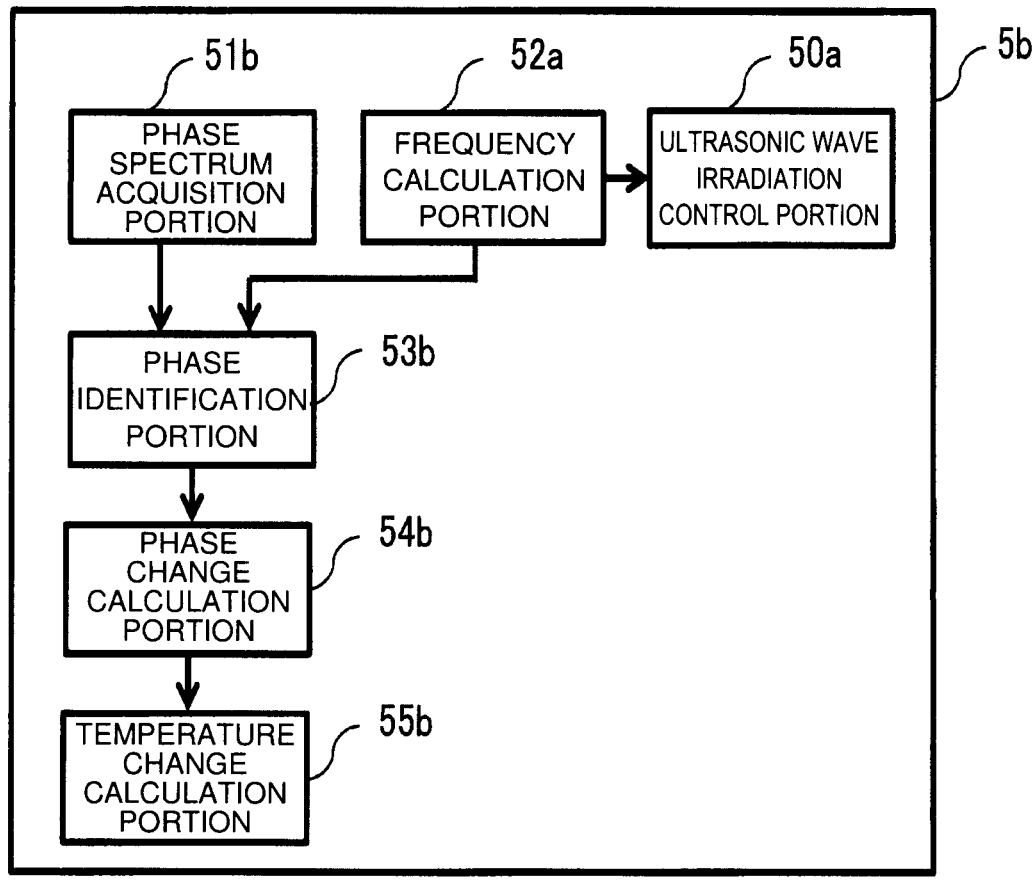
FIG. 15 is a block diagram showing a configuration example of a calculation unit of the in-vivo temperature measurement device according to the third embodiment of the present invention.

FIG. 14 is a flowchart for describing an operation of the in-vivo temperature measurement device 1b of the present embodiment, and FIG. 15 is a block diagram showing a configuration example of the calculation unit 5b of the present embodiment. The calculation unit 5b includes an ultrasonic wave irradiation control portion 50a, a phase spectrum acquisition portion 51b, a frequency calculation portion 52a, a phase identification portion 53b, a phase change calculation portion 54b, and a temperature change calculation portion 55b.

Operations (steps S300 and S301 in FIG. 14) of the frequency calculation portion 52a and the ultrasonic wave irradiation control portion 50a of the calculation unit 5b are as described in steps S200 and S201.

The lock-in detector (phase amplifier) can detect not only an amplitude but also a phase by an angular frequency at the same time. Therefore, the lock-in detector 4b of the present embodiment detects a phase of the ultrasonic wave reception signal having the above-described repetition frequency from the ultrasonic wave reception signals obtained by the ultrasonic wave detection unit 3 (step S302 in FIG. 14).

In this way, by emitting the ultrasonic wave while sweeping the repetition frequency to detect phase of the ultrasonic wave reception signal at each repetition frequency and collecting a phase value to be sequentially output from the lock-in detector 4b, the phase spectrum acquisition portion 51b can acquire a phase spectrum of the ultrasonic wave reception signal (step S304 in FIG. 14).

Figure 16:
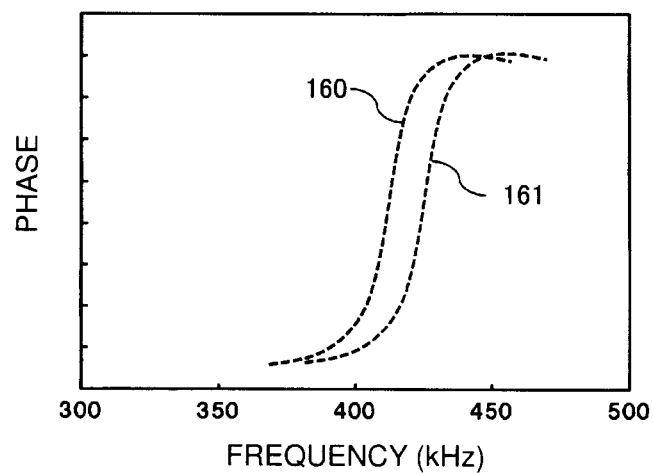
FIG. 16 is a view showing an example of a phase spectrum of an ultrasonic wave reception signal.

FIG. 16 shows an example of the phase spectrum of the ultrasonic wave reception signal acquired by the phase spectrum acquisition portion 51b. A phase spectrum denoted by 160 in FIG. 16 indicates a phase spectrum before the temperature inside the living body 10 changes, and a phase spectrum denoted by 161 in FIG. 16 indicates a phase spectrum after the temperature inside the living body 10 changes.

Next, the phase identification portion 53b of the calculation unit 5b identifies a phase φ of a peak frequency of the amplitude spectrum, from the phase spectrum acquired by the phase spectrum acquisition portion 51b (step S305 in FIG. 14). Specifically, the phase identification portion 53b may identify a phase of an inflection point of the phase spectrum as the phase φ of the peak frequency of the amplitude spectrum. Then, the calculation unit 5b returns to step S301 when the identification of the phase p in step S305 has not been completed twice (NO in step S306 in FIG. 14). In this way, the processes of steps S301 to S305 are repeated twice.

The phase change calculation portion 54b of the calculation unit 5b calculates the amount of phase change Δφ of the peak frequency, that is, a difference Δφ(=φ2−φ1) between a phase φ2 of a second peak frequency and a phase φ1 of a first peak frequency obtained by the phase identification portion 53b (step S307 in FIG. 14).

Then, the temperature change calculation portion 55b of the calculation unit 5b calculates, from the amount of phase change Δφ of the peak frequency, the amount of temperature change ΔT in the living body 10 using the following formula (step S308 in FIG. 14).

Formula 4

$$\Delta\phi = K\Delta T \tag{4}$$

In Formula (4), K is a fixed number. The fixed number K is registered in the storage unit 6 in advance. Note that the value of the fixed number K can be determined by, for example, previous experiment in which a probe of a thermometer is inserted into the living body to obtain a change in deep body temperature.

The value of the amount of temperature change ΔT calculated by the temperature change calculation portion 55b is transmitted to the outside via the communication unit 7. The in-vivo temperature measurement device 1b repeats the processes of steps S301 to S308 until a user gives an instruction to stop the measurement, for example. Thus, it is possible to obtain an effect of the present embodiment similar to that of the first embodiment.

In the first to third embodiments, the in-vivo temperature measurement device 1, 1a, or 1b is disposed on the back of the living body 10 (human body) as an example, but the in-vivo temperature measurement device 1, 1a, or 1b may be disposed to contact with, for example, a front arm of the living body 10 without being limited thereto. In this case, the distance L between the structures in the living body 10 may be a distance between the radius and the ulna.

In the in-vivo temperature measurement devices 1, 1a, and 1b described in the first to third embodiments, the calculation units 5, 5a, and 5b and the storage unit 6 can be realized by a computer including a CPU (Central Processing Unit), a storage device, and an interface and a program for controlling these hardware resources. The CPU executes the processes described in the first to third embodiments according to the program stored in the storage device.

INDUSTRIAL APPLICABILITY

Embodiments of the present invention are applicable to a technique for detecting a temperature change in a living body.

REFERENCE SIGNS LIST 1, 1a in-vivo temperature measurement device
2 ultrasonic wave irradiation unit
3 ultrasonic wave detection unit
4 amplifier
4a, 4b lock-in detector 5, 5a, 5b calculation unit
6 storage unit
7 communication unit
10 living body
50, 50a ultrasonic wave irradiation control portion
51 frequency analysis portion
51a amplitude spectrum acquisition portion
51b phase spectrum acquisition portion
52, 52a frequency calculation portion
53 frequency identification portion
53b phase identification portion
54 frequency change calculation portion
54b phase change calculation portion
55, 55b temperature change calculation portion.

The invention claimed is:

1. An in-vivo temperature measurement device comprising:
an ultrasonic wave irradiator that irradiates a living body with a first ultrasonic wave and a second ultrasonic wave;
an ultrasonic wave detector that receives a third ultrasonic wave reflected by the living body in response to the first ultrasonic wave and a fourth ultrasonic wave reflected by the living body in response to the second ultrasonic wave;
a frequency calculator that calculates a frequency of a fifth ultrasonic wave amplified in the living body based on information regarding a structure of the living body;
a frequency analyzer that:
performs frequency analysis on the third ultrasonic wave and the fourth ultrasonic wave; and
acquires a first amplitude spectrum of the third ultrasonic wave and a second amplitude spectrum of the fourth ultrasonic wave;
a frequency identifier that identifies, from the first amplitude spectrum and the second amplitude spectrum, a first peak frequency of the first amplitude spectrum that is closest to the frequency calculated by the frequency calculator and second peak frequency of the second amplitude spectrum that is closest to the frequency calculated by the frequency calculator;
a frequency change calculator that calculates an amount of frequency change, from the first peak frequency and the second peak frequency; and
a temperature change calculator that calculates an amount of temperature change in the living body from the amount of frequency change.

2. The in-vivo temperature measurement device of claim 1, wherein the frequency identifier identifies the first peak frequency prior to the ultrasonic wave irradiator irradiating the living body with the second ultrasonic wave.

3. The in-vivo temperature measurement device of claim 1, wherein the frequency calculator is configured to calculate the frequency of the fifth ultrasonic wave amplified in the living body, based on the information on the structure of the living body and a value of a sound speed in the living body, and wherein the value of the sound speed is registered in advance of calculating the frequency of the fifth ultrasonic wave.

4. The in-vivo temperature measurement device of claim 1, the information on the structure of the living body is a distance between structures in the living body.

5. An in-vivo temperature measurement device comprising:
an ultrasonic wave irradiator that irradiates a living body with a first ultrasonic waves and a second ultrasonic waves;
an ultrasonic wave detector that receives a third ultrasonic wave reflected by the living body in response to the first ultrasonic wave and a fourth ultrasonic wave reflected by the living body in response to the second ultrasonic wave;
a frequency calculator that calculates a frequency of a fifth ultrasonic wave amplified in the living body based on information regarding a structure of the living body;
an ultrasonic wave irradiation controller that sweeps a repetition frequency at which the first ultrasonic wave is emitted from the ultrasonic wave irradiator within a predetermined range centered on the frequency calculated by the frequency calculator;
a lock-in detector that detects a sixth ultrasonic wave and a seventh ultrasonic wave each of the repetition frequency from the third ultrasonic wave and the fourth ultrasonic wave received by the ultrasonic wave detector;
an amplitude spectrum acquirer that collects amplitude values of signals sequentially output from the lock-in detector and acquires a first amplitude spectrum of the sixth ultrasonic wave and a second amplitude spectrum of the seventh ultrasonic wave;
a frequency identifier that identifies, from the first amplitude spectrum and the second amplitude spectrum, a first peak frequency of the first amplitude spectrum that is closest to the frequency calculated by the frequency calculator and second peak frequency of the second amplitude spectrum that is closest to the frequency calculated by the frequency calculator;
a frequency change calculator that calculates an amount of frequency change, from the first peak frequency and the second peak frequency; and
a temperature change calculator that calculates an amount of temperature change in the living body from the amount of frequency change.

6. The in-vivo temperature measurement device of claim 5, wherein the frequency calculator is configured to calculate the frequency of the fifth ultrasonic wave amplified in the living body, based on the information on the structure of the living body and a value of a sound speed in the living body, and wherein the value of the sound speed is registered in advance of calculating the frequency of the fifth ultrasonic wave.

7. The in-vivo temperature measurement device of claim 5, the information on the structure of the living body is a distance between structures in the living body.

8. An in-vivo temperature measurement device comprising:
an ultrasonic wave irradiator that irradiates a living body with a first ultrasonic wave;
an ultrasonic wave detector that receives ultrasonic waves reflected by the living body;
a frequency calculator that calculates, based on information on a structure of the living body, a frequency of a second ultrasonic wave amplified in the living body;
an ultrasonic wave irradiation controller that sweeps a repetition frequency at which the first ultrasonic wave is emitted from the ultrasonic wave irradiator within a predetermined range centered on the frequency calculated by the frequency calculator;
a lock-in detector that detects a phase of an ultrasonic wave of the repetition frequency from the ultrasonic waves received by the ultrasonic wave detector;

a phase spectrum acquirer that collects phase values sequentially output from the lock-in detector and acquires a respective phase spectrum each of the ultrasonic waves;

a phase identifier that identifies, from phase spectrums of the ultrasonic waves, a respective phase of a respective peak frequency of a respective amplitude spectrum of each of the ultrasonic waves;

a phase change calculation portion that calculates an amount of phase change from phases of two peak frequencies of the ultrasonic waves obtained by sweeping the repetition frequency twice; and a temperature change calculation portion that calculates an amount of temperature change in the living body from the amount of phase change.

9. The in-vivo temperature measurement device of claim 8, wherein the frequency calculator is configured to calculate the frequency of the second ultrasonic wave amplified in the living body, based on the information on the structure of the living body and a value of a sound speed in the living body, and wherein the value of the sound speed is registered in advance of calculating the frequency of the second ultrasonic wave amplified in the living body.

10. The in-vivo temperature measurement device of claim 8, the information on the structure of the living body is a distance between structures in the living body.

* * * * *